United States Patent
Farrukh et al.

(10) Patent No.: US 9,555,009 B2
(45) Date of Patent: Jan. 31, 2017

(54) CIPROFLOXACIN LOADED DIETHYLAMINOETHYL CELLULOSE NANOPARTICLES

(71) Applicants: Muhammad Akhyar Farrukh, Lahore (PK); Muhammad Rehan Gul, Lahore (PK); Muhammad Khaleeq-ur-Rahman, Lahore (PK)

(72) Inventors: Muhammad Akhyar Farrukh, Lahore (PK); Muhammad Rehan Gul, Lahore (PK); Muhammad Khaleeq-ur-Rahman, Lahore (PK)

(*) Notice: Subject to any disclaimer, the term of this patent is extended or adjusted under 35 U.S.C. 154(b) by 3 days.

(21) Appl. No.: 14/516,824

(22) Filed: Oct. 17, 2014

(65) Prior Publication Data
US 2016/0106685 A1    Apr. 21, 2016

(51) Int. Cl.
*A61K 9/51*     (2006.01)
*A61K 31/496*   (2006.01)
*A61K 31/00*    (2006.01)

(52) U.S. Cl.
CPC ........... *A61K 9/5192* (2013.01); *A61K 9/5161* (2013.01); *A61K 31/00* (2013.01); *A61K 31/496* (2013.01)

(58) Field of Classification Search
None
See application file for complete search history.

(56) References Cited

U.S. PATENT DOCUMENTS

| | | | |
|---|---|---|---|
| 2006/0165987 A1* | 7/2006 | Hildgen et al. | 428/402.2 |
| 2010/0009007 A1* | 1/2010 | Darvari et al. | 424/499 |
| 2010/0323014 A1* | 12/2010 | Bloom et al. | 424/486 |
| 2013/0089599 A1* | 4/2013 | DeSilva et al. | 424/450 |

* cited by examiner

*Primary Examiner* — Robert A Wax
*Assistant Examiner* — Randeep Singh
(74) *Attorney, Agent, or Firm* — Sarfaraz K. Niazi

(57) ABSTRACT

This invention reports ciprofloxacin (CIP)-encapsulated polymeric nanoparticles and its antibacterial potential with a variety of gram positive and gram negative pathogenic bacteria. CIP-encapsulated nanoparticles of diethylaminoethyl cellulose (DEA-EC) are prepared by the multiple emulsion solvent evaporation method. CIP-encapsulated nanoparticles showed superior effectiveness to inhibit the growth of bacteria in-vitro.

8 Claims, 15 Drawing Sheets

CIPROFLOXACIN LOADED DIETHYLAMINOETHYL CELLULOSE NANOPARTICLES

BACKGROUND OF THE INVENTION

Fluoroquinolones are the most famous antibacterial drugs due to their therapeutic effectiveness having tolerable side effects and provide better treatment which is becoming more prone to the beta lactam antibiotics which are not effective against resistant pathogenic bacteria. The fluoroquinolone include norfloxacin, ofloxacin, ciprofloxacin, etc. The benzopyridone nucleus (quinolone) provide various chemical sites for attachment of functional groups which enhance the antibacterial activity, and the discovery of fluorine atom and piperazinyl ring on the quinolone ring completely changed the medicinal chemistry and the clinical importance of fluoroquinolones.

BRIEF SUMMARY OF THE INVENTION

Ciprofloxacin (FIG. 1), which has an N-1-cyclopropyl group, is the most potent of the marketed flouroquinolones in vitro against a wide variety of gram positive and gram negative bacteria. The fluorine group at position C— improves the DNA gyrase complex binding (up to 17 times), and cell penetration (up to 70 times) of the relevant derivatives with no substitution at the C-6 position. Due to marked enhancement of antibacterial potency, most of the newly synthesized quinolones contain a C-6 fluorine substituent.

Recently, drug delivery with nanoparticles have been shown to improve the delivery of drugs to the target tissue of interest. Most of the antibacterial drugs available in the market are poorly water soluble and have poor pharmacokinetic performance. One solution is to formulate these drugs into nanoparticles, which can be either crystalline or amorphous prior to delivery. Rapid drug dissolution can be achieved by reducing the drug size which increases the drug's surface area for absorption and it greatly increases the bioavailability of the drug and as a result have better therapeutic responses.

The main objective in designing the drug loaded polymeric nanoparticles is to achieve the controlled release of a drug from the polymer and increase the surface area of a drug by decreasing its size and deliver the drug to the exact targeted site of action. Pharmaceutical properties of polymeric nanoparticles, including carrier nature, particle size and size distribution, surface and bulk morphology, surface chemistry, surface charge, thermogram property, drug encapsulation efficiency (EE) and drug release kinetics of the particles must be assessed before formulation. These parameters have a great effect on the in-vivo drug pharmacokinetics and the distribution of a drug loaded in the nanoparticles to the target tissues. For formulating polymeric nanoparticles, the solvent extraction/evaporation method is one of the most widely employed techniques and poly vinyl alcohol (PVA) is the most commonly used emulsifier in the process.

Present research focuses on the development of novel nanobiopharmaceutical dosage forms with nanocapsules and nanospheres formation by a solvent evaporation method by using diethylaminoethyl cellulose as and polyvinyl alcohol as a polymer. Its characterization performed along with detailed antimicrobial activity in comparison to the commercially available dosage form of ciprofloxacin. Stability and dissolution studies were performed, enhanced in-vitro antibacterial activity was observed.

DETAILED DESCRIPTION OF THE INVENTION

Materials and Methods

Diethylaminoethyl cellulose (DEA-EC) was purchased from Sigma Aldrich. Poly vinyl alcohol (PVA, MW 15,000 g/mol) was purchased from Sigma Aldrich. Ethyl acetate as a HPLC grade was purchased from Aldrich. Ciprofloxacin was received as a gift from Highnoon pharmaceutical private limited Lahore Pakistan.

1.1. Preparation of CIP-Encapsulated DEA-EC Polymeric Nanoparticles by Solvent Evaporation Method Solvent evaporation was the foremost method devised to formulate the polymeric nanoparticles. In this method, polymer solutions are made in volatile solvents and emulsions are obtained. In the past, dichloromethane and chloroform volatile solvents were mostly used, but they are now replaced with ethyl acetate which has a better toxicological profile. The emulsion obtained is converted into a nanoparticle suspension on evaporation of the solvent for the polymer, which diffuses between the continuous phases of the emulsion.

Figure 1:
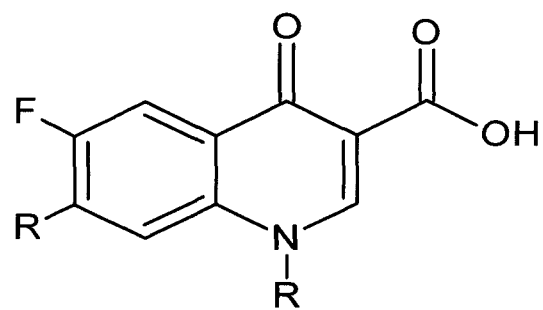
FIG. 1 depicts Ciprofloxacin chemical structure.
Figure 2:
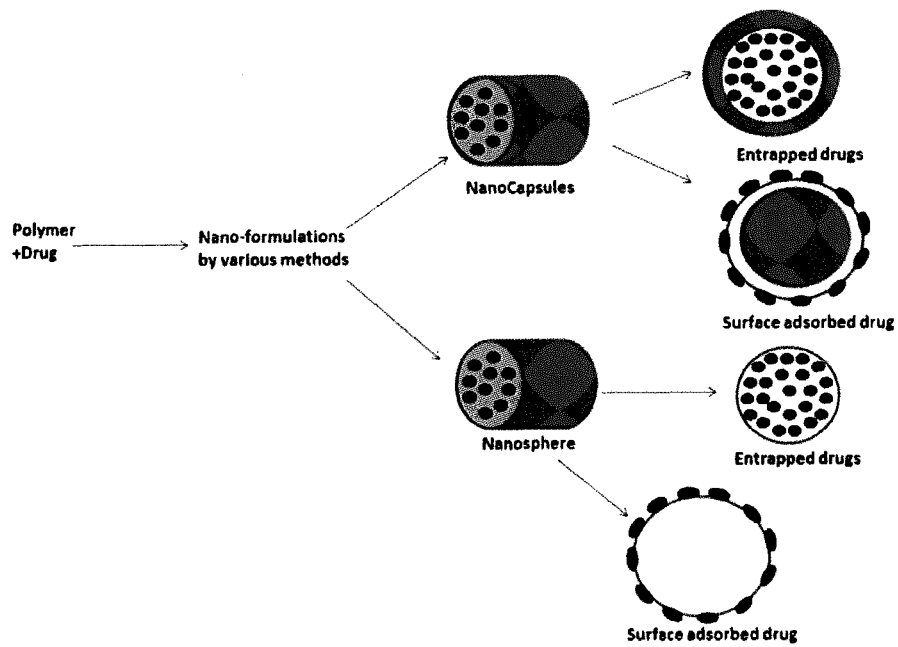
FIG. 2 depicts types of drug nanoparticles according to a structural organization.

There are two main strategies used for the formation of emulsions, the preparation of single emulsions, e.g., oil-in-water (o/w) or double-emulsions, e.g., water-in-oil-in-water (w/o/w). These methods involve the utilization ultrasonication, followed by evaporation of the solvent by continuous magnetic stirring at room temperature. Afterwards, the solidified nanoparticles can be collected by ultracentrifugation and washed with distilled water to remove additives. According to the structural organization biodegradable nanoparticles are classified as nanocapsule, and nanosphere. The drug molecules are either entrapped inside or adsorbed on the surface (FIG. 2).

Volatile organic solvent ethyl acetate was taken 7 mL in 50 mL beaker and added 80 mg diethylaminoethyl cellulose (DEA-EC) polymer into it and magnetically stirred for 20 minutes at medium rpm aqueous solution of pure ciprofloxacin 4 mg/mL was added drop wise after 1 minute interval per drop into above volatile mixture on magnetic stirring. In another beaker 0.1 grams of polyvinyl alcohol was added in 10 mL distilled water and magnetically stirred at high rpm for 30 minutes. Added drop wise volatile mixture containing drug into the 1% PVA solution and continued stirring for 30 minutes until homogeneous emulsion formed. Then ultrasonicated in perkin elmer bath sonicator 60 Hz for 20 minutes.

Figure 3:
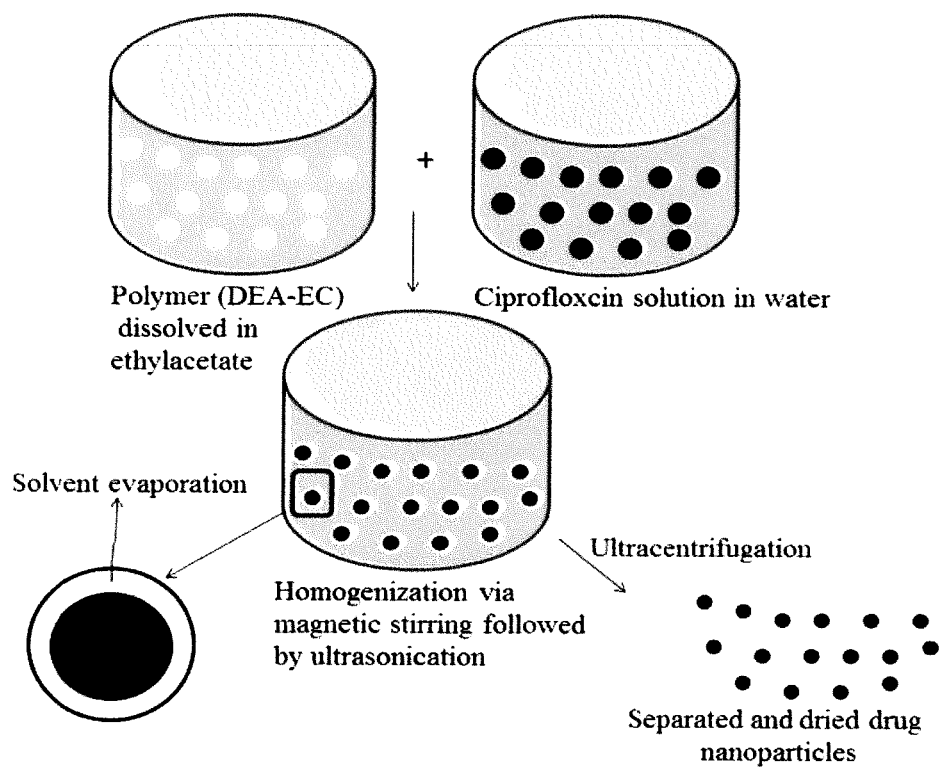
FIG. 3 depicts the solvent evaporation method.

After ultrasonication, kept it stirring on magnetic stirrer hot plate for 20 minutes, ultracentrifuged the above obtained nanoemulsion at 13000 rpm for 10 minutes and settled material was subjected to drying in oven at 50° C. for 1 hour. Dried powder obtained was stored in closed vial. A brief description of the method is given in FIG. 3.

1.2. Mechanism of Drug Release from Polymer

Figure 4:
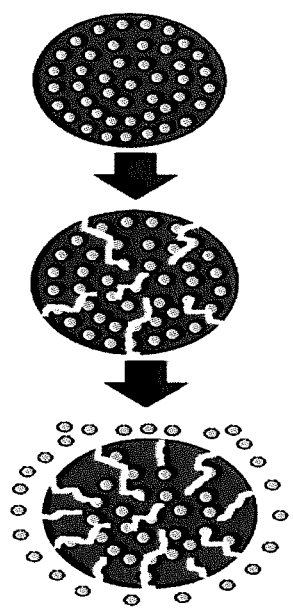
FIG. 4 depicts a mechanism of drug release from polymer.
Figure 5A:
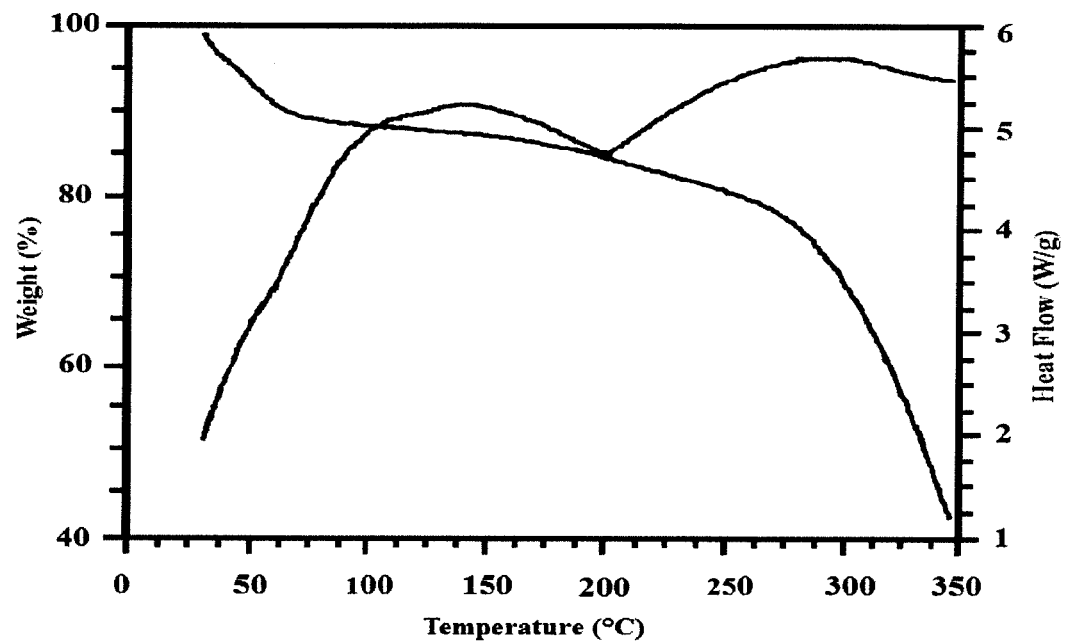
FIG. 5A depicts DSC-TGA of Ciprofloxacin loaded DEA-EC nanoparticles.
Figure 5B:
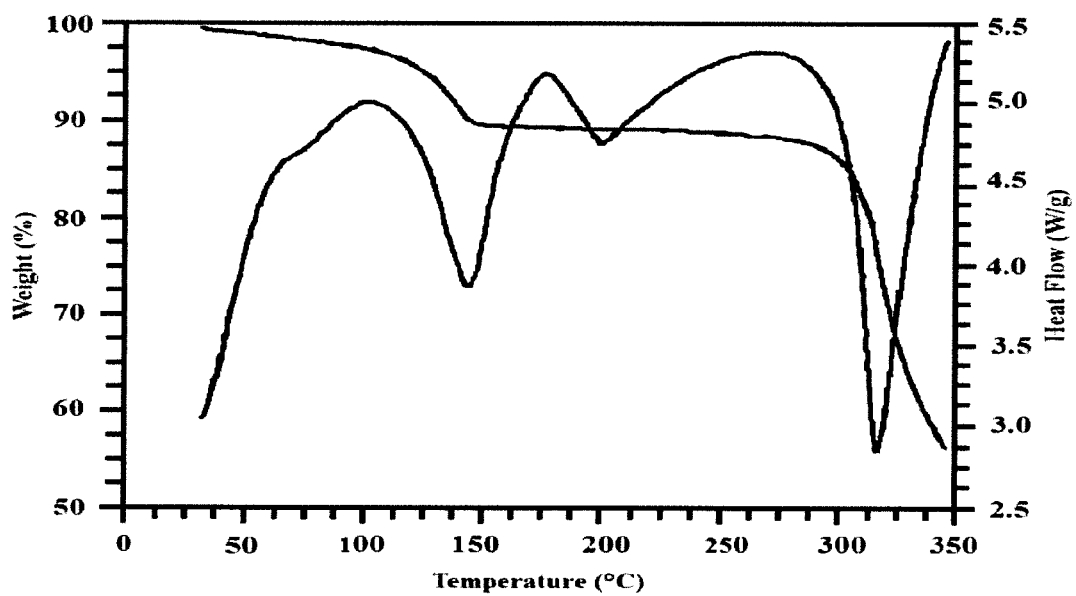
FIG. 5B depicts DSC-TGA of pure ciprofloxacin.
Figure 5C:
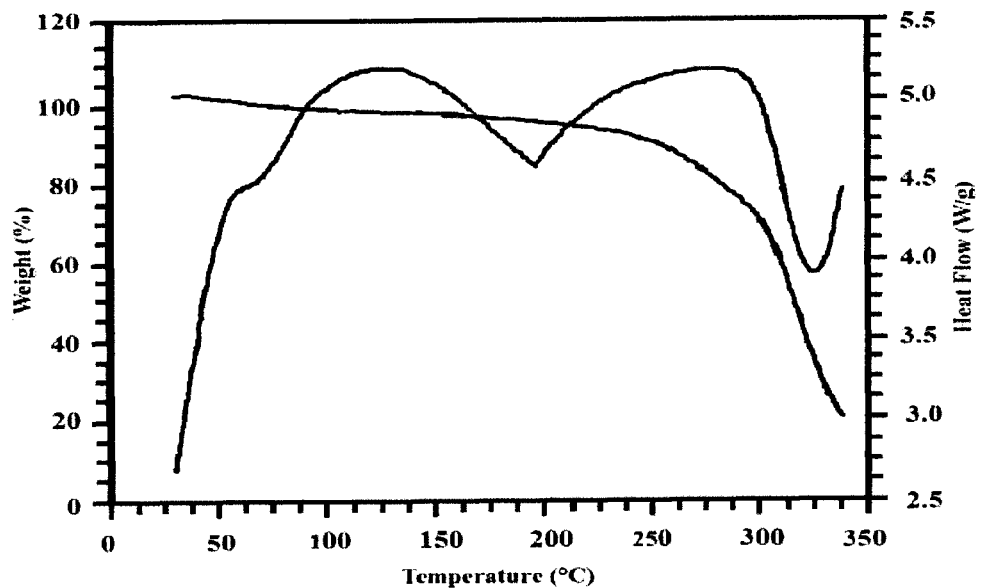
FIG. 5C depicts DSC-TGA of DEA-EC.
Figure 5D:
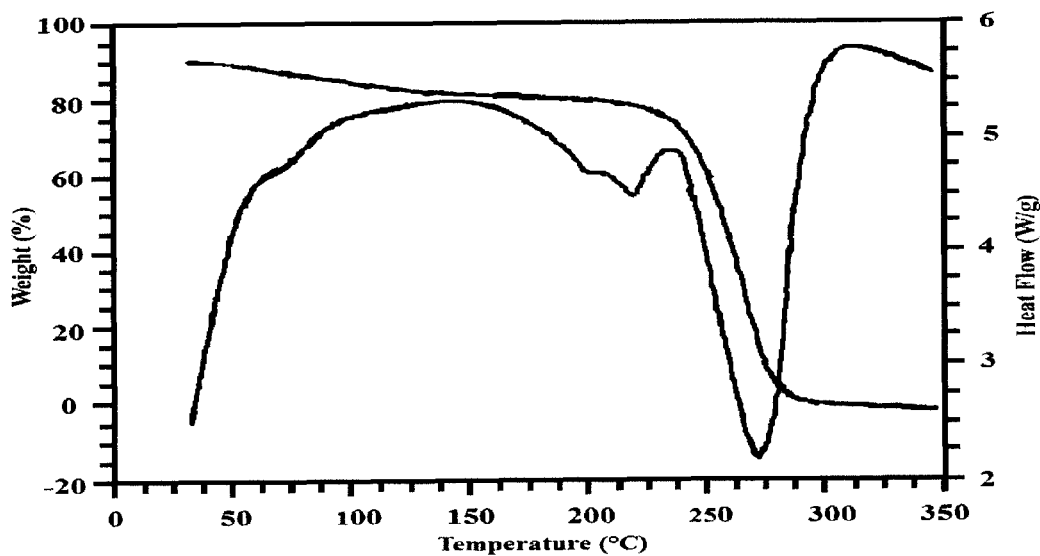
FIG. 5D depicts DSC-TGA of Poly vinyl alcohol.

When polymer erodes in body (FIG. 4) due to enzymes action, cracks are formed and cracks become further apart and ultimately drug particles in nano form are released one after the other.

1.3. Drug Loading Efficiency and Drug Contents in Ciprofloxacin Loaded DEA-EC Nanoparticles To determine the ciprofloxacin content in nanoparticles, 7 mg of nanoparticles were dissolved in 7 mL of dichloromethane and then 5 mL of deionized water was added. This mixture was placed on magnetic stirrer for 7 hours and 1 mL was withdrawn to measure the drug contents. Absorbance was measured for this 1 mL in UV-Spectrophotometre (Schimadzu 1601) at 278 nm. Drug contents and loading efficiency were calculated by following formulae $$\text{Drug Contents} = \left[\frac{\text{Drug weight in nanoparticles}}{\text{total weight in nanoparticles}}\right] \times 100$$

$$\text{Loading Efficiency} = \left[\frac{\text{Drug remaining in nanoparticles}}{\text{feeding weight in drugs}}\right] \times 100$$

1.4. Stability Studies

Ciprofloxacin loaded DEA-EC loaded nanoparticles were subjected to stability testing in stability chambers. Cincinnati sub-zero (CSZ) stability chamber was used which is ideal for ICH Q1A standards stability testing, shelf life, package testing, accelerated aging. The drug loaded DEA-EC nanoparticles and nanosuspension were placed in stability chamber for analyzing stability in variety of storage conditions.

1.5. TGA-DSC of Ciprofloxacin Encapsulated Polymeric Nanoparticles

TGA DSC analysis was performed on the formed nanoparticles to check thermal degradation pattern of the drug and thermal stability of biopolymer. Analysis was performed on Q600 TGA DSC Instrument and Ramp rate was 50° C. and maximum temperature was set at 500° C. Ciprofloxacin pure, PVA and polymer DEA-EC were subjected to the analysis and results analyzed.

1.6. FTIR of Ciprofloxacin Encapsulated Polymeric Nanoparticles

FTIR of ciprofloxacin nanoparticles along with Ciprofloxacin pure, PVA and polymer DEA-EC were subjected to the analysis and results analyzed. Bruker alpha platiniun ATR was used for FTIR investigations.

1.7. Atomic Force Microscopy AFM of Ciprofloxacin Nanoparticles

Ciprofloxacin nanoparticles were subjected to atomic force microscopy on SPM-9700 instrument to check surface morphology of samples at the atomic level with a three dimensional view, two dimensional view and roughness and to analyze the sample in any kind of environment.

1.8. HPLC of Ciprofloxacin Nanoparticles

The HPLC analysis was carried out with a Agilent 1200 system, Agilent Programmable Absorbance Detector and Agilent Chem Station software for HPLC system.

1.9. Antibacterial Activity of Ciprofloxacin Nanoparticle

Antibacterial activity was studied by using Kirby Buyer analysis and zone of inhibition were calculated. Antibacterial activity was studied against Gram-positive coverage includes penicillinase- and non-penicillinase producing *Staphylococci, Streptococcus pneumoniae* and viridans, *Enterococcus faecalis, Listeria monocytogenes*, and *Nocardia* species. Gram negative coverage includes *Neisseria meningitides* and *gonorrhoeae, Haemophilus* influenza, and most clinically important Enterobacteriaceae species, *Pseudomonas aeruginosa* and *Vibrio* species.

1.10. Zeta Potential Calculation of Nanoparticles

Zetasizer Nano Z instrument was used to calculate the zeta potential of ciprofloxacin loaded DEA-EC nanoparticles.

1.11. XRD Analysis

XRD measurements were obtained powder diffraction system powder X-ray diffractrometer (XRD) using 83 PAN analytical MPD XPERT PRO. 10 mg of each sample was scanned from 10° to 70° (2θ). The samples were scanned at 25° C.

1.12. Scanning Electron Microscope

Ciprofloxacin loaded nanoparticles were analyzed by the Hitachi S-3400 Variable Pressure SEM at 10-15 kV and resolution up to 50-100 μm.

1.13. GCMS Analysis

GC-MS analysis of pure ciprofloxacin and ciprofloxacin in nanoparticles form was performed using a Shimadzu model 92 QP-2010 instrument. Comprising sampling port and a gas chromatograph interfaced to a mass spectrometer (GC-MS).

1.14. Dissolution Studies

The in-vitro dissolution profiles of ciprofloxacin were studied in the dissolution media using US Pharmacopoeia (USP) Apparatus II. Pharma tester hainberg Germany instrument. In order to check the rate of dissolution, samples were withdrawn from the dissolution medium for quantification over nine pre-determined time points during a total period of eight hours. Samples were analyzed by an UV spectrophotometer at 278 nm for confirmation.

1.15. TGA-DSC of Ciprofloxacin Loaded Nanoparticles

DSC scan of the ciprofloxacin (FIG. 5) shows two endothermic transitions. The first broad peak with the onset temperature of 145° C. was attributed to the dehydration process. This was confirmed by corresponding weight loss at the same temperature range during TGA scans. The second endotherm at 314 C was due to melting of the dehydrated phase. DSC scan of Ciprofloxacin loaded polymeric nanoparticles sample shows mild endothermic peak at 203° C. This corresponds to the fact that Ciprofloxacin is entrapped in polymer, DEA-EC which also shows same endothermic peak when analyzed separately i.e. at 203° C. TGA curve of pure ciprofloxacin and cipro Nano particles when compared it indicates the stability in nano form because it is entrapped in DEA-EC polymer. There is weight loss initially of 5% age at 59° C. that corresponds to loss of water molecules attached with ciprofloxacin hydrated molecule. Degradation started at 275° C., before which there was no change in TGA curve. That indicates the stability of nanoparticles. Ciprofloxacin has melting point of 257° C.

1.16. Fourier Transform Infra-Red Spectroscopy (FTIR)

Figure 6A:
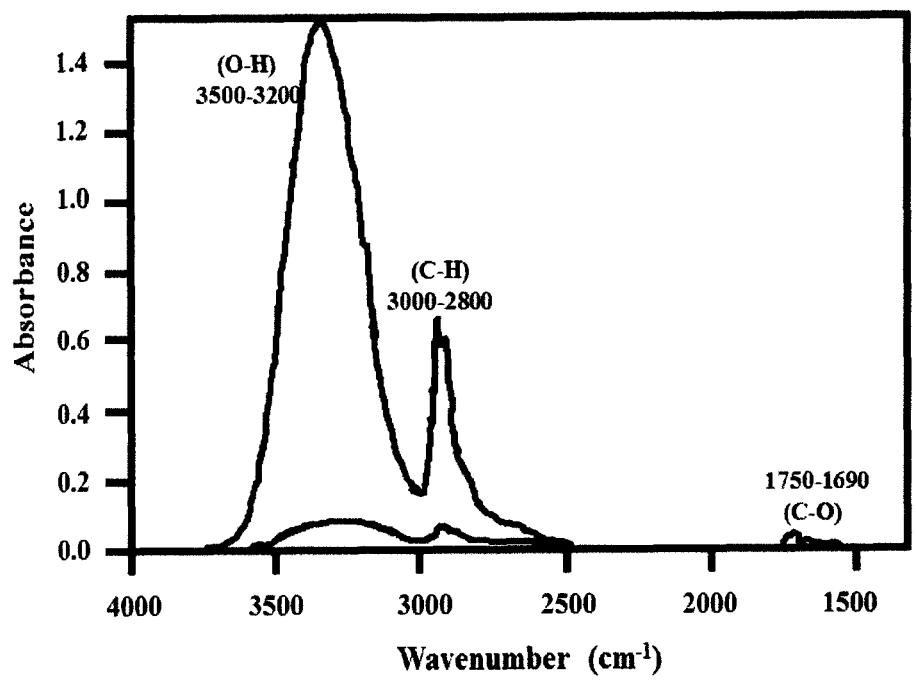
FIG. 6A depicts FTIR spectra of PVA.

FIG. 6A indicates large bands between 3500-3200 $cm^{-1}$ are linked to the stretching O—H from the intermolecular and intramolecular hydrogen bonds. The vibration band between 3000-2800 $cm^{-1}$ refers to the stretching C—H from alkyl groups, and the peaks between 1750-1690 $cm^{-1}$ are due to the stretching C═O and C—O from acetate group remaining from Poly Vinyl Alcohol (PVA).

Figure 6B:
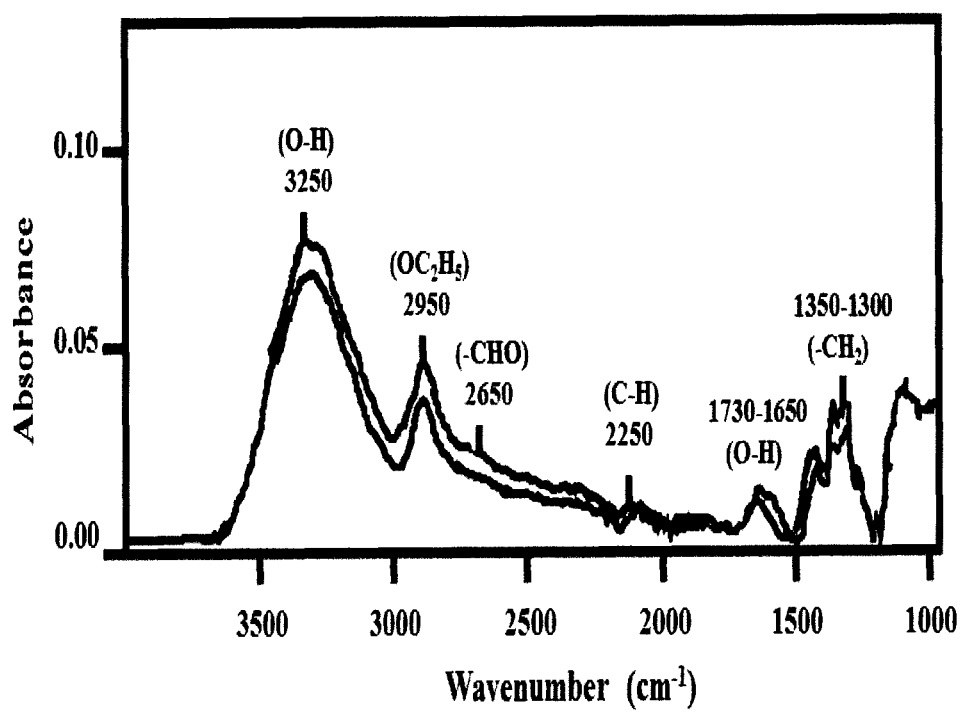
FIG. 6B depicts FTIR spectra of diethylaminoethyl cellulose.

FIG. 6B indicates peaks between 3500-3300 $cm^{-1}$ is of —OH groups present on the closed ring structure of the polymer repeating units. It is also likely that the polymer may have some absorbed water already, due to its hydrophilic nature. The same also represents intra and intermolecular hydrogen bonding due to the —OH groups. The shoulder peak at 3250 $cm^{-1}$ corresponds to associate —OH of intermolecular bonding. The small but not sharp peak at 2950 $cm^{-1}$ corresponds to asymmetric structure vibrations of the —$OC_2H_5$ ethoxy groups. There are small peaks between 2850 and 2720 $cm^{-1}$ corresponding to —CHO stretching, which is sharp at 2650 $cm^{-1}$. The peaks and valleys between 2000 and 2250 $cm^{-1}$ are of the —CH stretching (of the saturated ring structure). The peaks at 1730 and 1650 $cm^{-1}$ are for bending of the —OH group structure. The 1350 and 1300 $cm^{-1}$ responses are due to the —$CH_2$ bending vibrations indicates diethylaminoethyl cellulose.

Figure 6C:
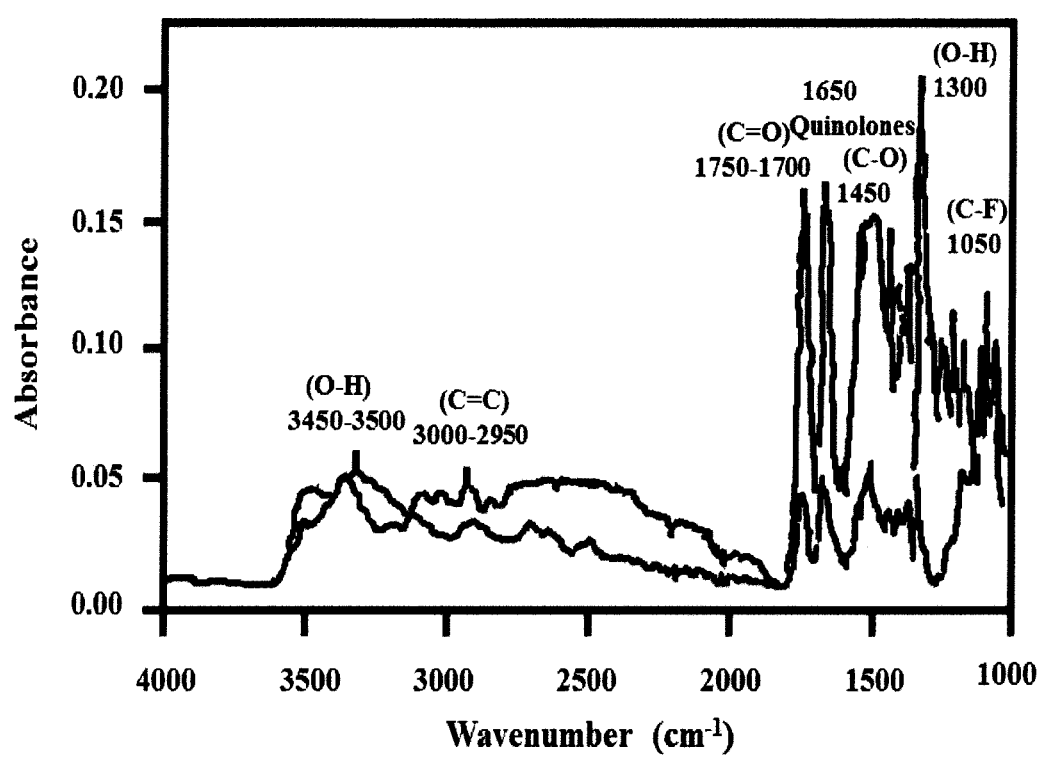
FIG. 6C depicts FTIR spectra of pure ciprofloxacin.

In FTIR spectra (FIG. 6C) of Ciprofloxacin, one prominent characteristic peak was found between 3500 and 3450 $cm^{-1}$, which was assigned to stretching vibration of OH groups and intermolecular hydrogen bonding. Another band at 3000-2950 $cm^{-1}$ represented alkene and aromatic C—H stretching, mainly $v^{═C—H}$. The 1950 to 1450 $cm^{-1}$ region exhibited FTIR absorption from a wide variety of double-bonded functional groups. The band at 1750 to 1700 $cm^{-1}$ represented the carbonyl C═O stretching i.e., $v^{C═O}$. The peak between 1650 and 1600 $cm^{-1}$ was assigned to quinolones. The band from 1450 to 1400 $cm^{-1}$ represented $v^{C—O}$ and at 1300 to 1250 $cm^{-1}$ suggested bending vibration of O—H group which proved the presence of carboxylic acid. A strong absorption peak between 1050 and 1000 $cm^{-1}$ was assigned to C—F group.

Comparison Between Ciprofloxacin and Ciprofloxacin Loaded Nanoparticles

Figure 7:
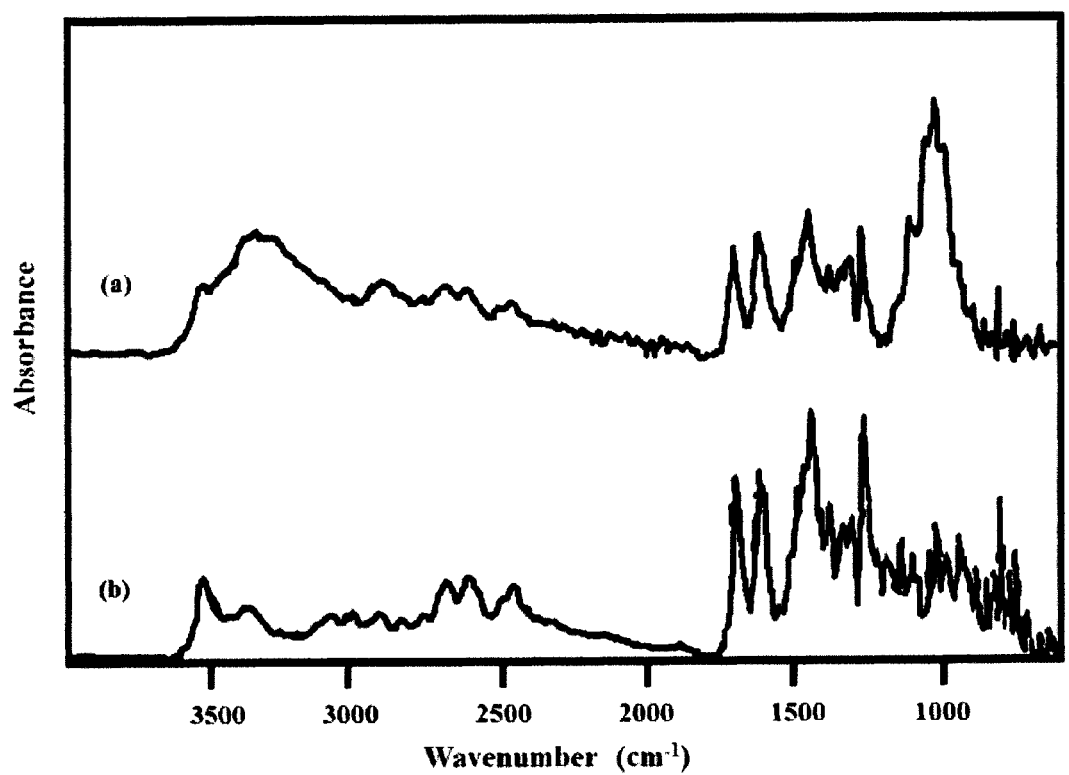
FIG. 7 depicts the FTIR spectra of ciprofloxacin nanoparticles and the FTIR spectra of pure ciprofloxacin.

Correlation calculated by BRUKA software (FIG. 7) for FTIR was 54.54% between pure ciprofloxacin and polymer entrapped ciprofloxacin in nano form. This comparison confirms the presence of ciprofloxacin in nano form polymeric nanocapsules/nanospheres.

1.17. Atomic Force Microscopy (AFM) of Ciprofloxacin Nanoparticles

Figure 8A:
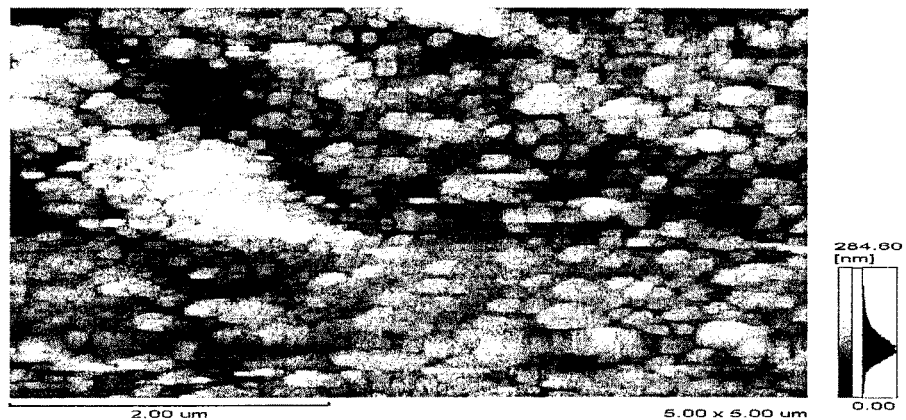
FIG. 8A depicts AFM Image in 2D of Ciprofloxacin.
Figure 8B:
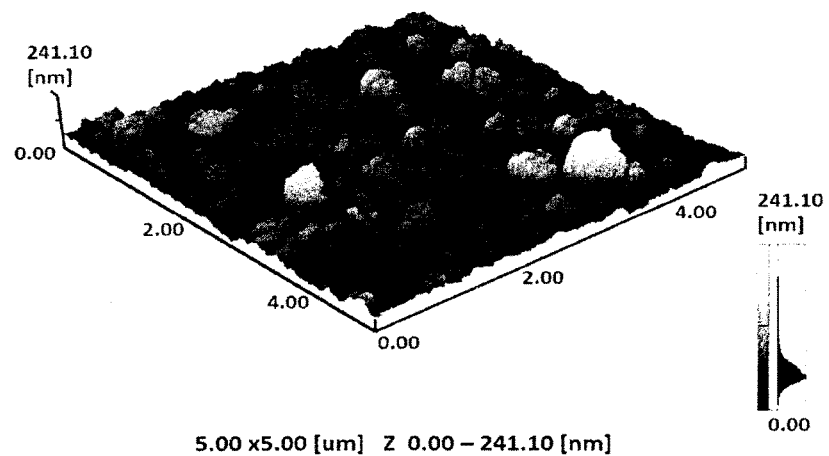
FIG. 8B depicts 3D of Ciprofloxacin.
Figure 8B:
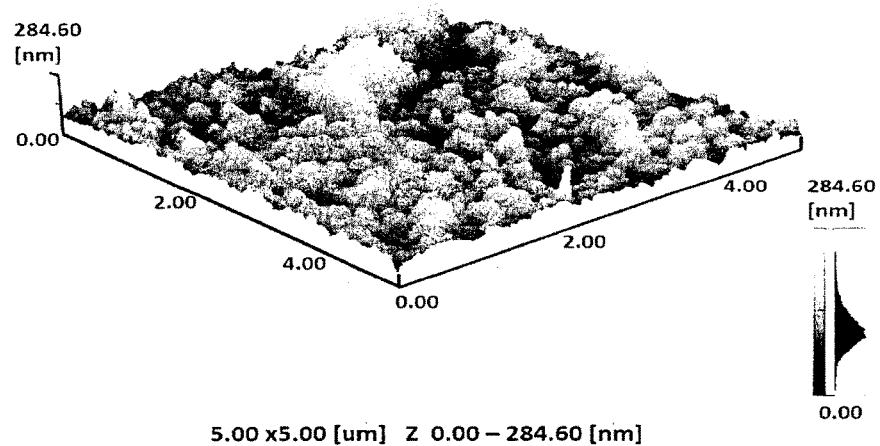
Figure 8C:
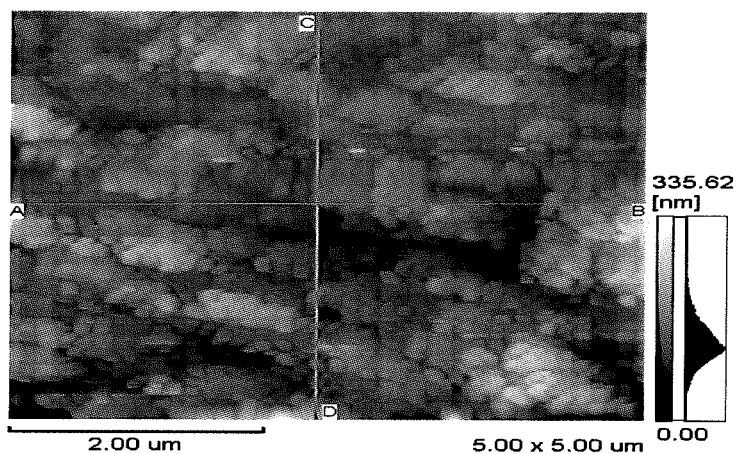
FIG. 8C depicts roughness of Ciprofloxacin.

Sample preparation for AFM, diluted in ethyl acetate was drop casted in a properly cleaned glass slide and well dried in air. From AFM images, 2 dimensional and 3 dimensional surface (FIGS. 8A, 8B and 8C) of ciprofloxacin nanoparticles is quite evident, structure is clustered grapes like morphology and average size distribution is 265 nm.

1.18. Drug Loading Efficiency and Drug Contents in Ciprofloxacin Loaded DEA-EC Nanoparticles Drug loading efficiency was calculated to be 55% w/w and drug contents were calculated 45% w/w. These results are due to Ciprofloxacin being a water soluble drug and it was released from the polymer DEA-EC during the solvent evaporation process.

1.19. HPLC of Ciprofloxacin Loaded Nanoparticles

The HPLC analysis was carried out with Agilent 1200 Series HPLC System. Agilent Chem Station software for LC system was employed. A simple HPLC method using only two solvents, 2% acetic acid aqueous solution and acetonitrile (ACN), with UV detection methodology for accurate determination of ciprofloxacin in Ciprofloxacin nanoparticles was used. The method employed reversed phase chromatography using a C18 column with an isocratic mobile phase of acetonitrile, 2% acetic acid aqueous solution (16:84, v/v). Umbelliferone was used as an internal standard, and a flow rate of 1.0 mL/min. The UV detector is set at 278 nm. The limit of detection is 0.25 µM (4 µm) guard column (Waters). Stock solutions of ciprofloxacin were prepared at 5.18 mM in 2% acetic acid aqueous solution. Umbelliferone was prepared at 6.17 mM in ACN. Solutions were kept at 4° C.

Figure 9:
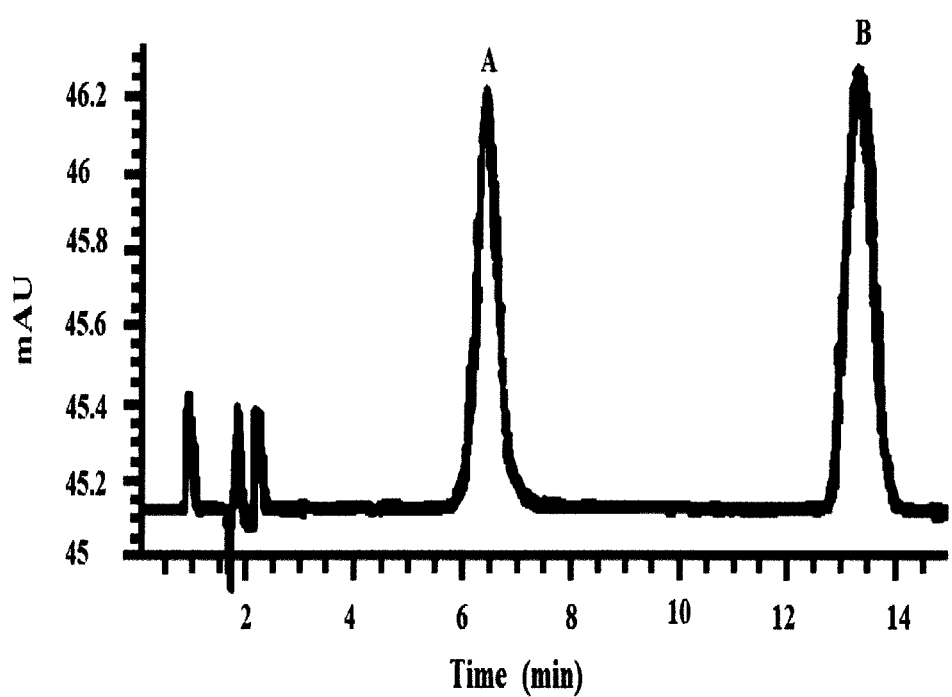
FIG. 9. depicts chromatogram showing retention time of ciprofloxacin and umbelliferone.

Peak of our active ingredient ciprofloxacin were sharp and detected by HPLC UV detection method. Peak A corresponds to ciprofloxacin and peak B at retention time 13 corresponds to the umbelliferone (FIG. 9). Ciprofloxacin detected at 278 nm UV detector, indicates formation of ciprofloxacin nanoparticles entrapped in DEA-EC coating. Drug polymeric complex is stable and no cross contamination occurred during synthesis and analysis.

1.20. Zeta Potential Measurement of Ciprofloxacin Nanoparticles

Zeta potential is forecasting tool for the colloidal stability. Nanoparticles with Zeta Potential values greater than +25 mV or less than −25 mV have high degrees of stability. Zeta potential for 3 samples was calculated as 23, 25 and 26 mV respectively. This indicates that nanoparticles formulated are stable, tend to aggregate after long time and flocculate, but on the whole the value calculated is hallmark of stability.

1.21. Dissolution Studies on Ciprofloxacin Nanoparticles

Figure 10:
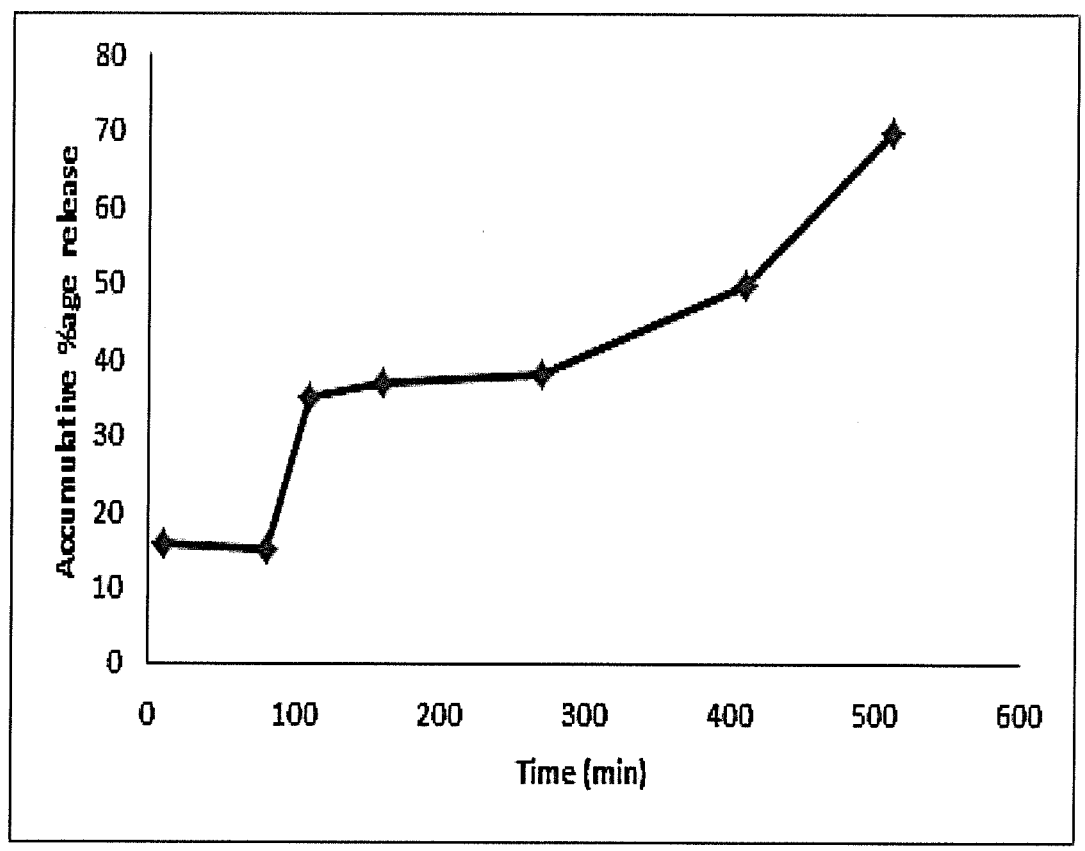
FIG. 10 depicts the percentage release of ciprofloxacin.

An accurately measured amount of ciprofloxacin nano-suspension equivalent to 3 mg ciprofloxacin suspended in 1 mL PBS (pH 7.4) in a glass cylinder having a length of 7 cm and diameter of 2 cm. This cylinder was fitted, before addition of nano suspension, with a pre-soaked dialysis membrane and was suspended in the dissolution flask of the United State Pharmacopeia (USP) dissolution tester (Pharma tester, Hainburg, Germany) containing 80 mL PBS (pH 7.4) and maintained at a temperature of 37° C. The glass cylinder was adjusted to rotate at a constant speed (80 rpm). At predetermined time intervals (0.5, 1, 1.5, −8 hours), 4 mL of the release medium withdrawn and assayed spectrophotometrically for drug content at 278 nm. Drug release detected till 8 hours (FIG. 10) that shows sustain release pattern of drug from nanoparticles and composition of drug complex didn't changed in that time period.

1.22. XRD of Ciprofloxacin and Ciprofloxacin Nanoparticles

Figure 11:
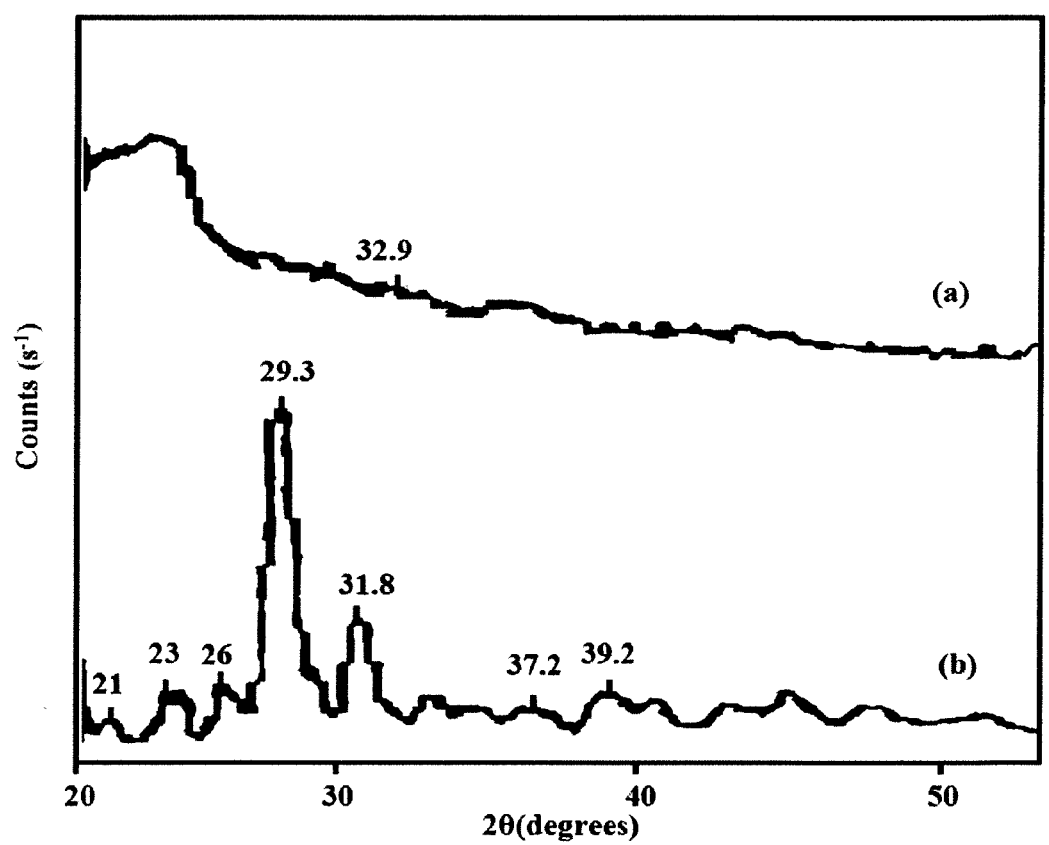
FIG. 11 depicts XRD spectra ciprofloxacin loaded DEA-EC nanoparticles and pure ciprofloxacin.

To study the characteristics of ciprofloxacin in the polymeric nanoparticles, XRD patterns (FIG. 11) were obtained using pure Ciprofloxacin and ciprofloxacin loaded DEA-EC nanoparticles. Main objective was to confirm the amorphous polymeric nanoparticles formed and crystallite of pure ciprofloxacin. Both samples were separately analyzed.

Each XRD pattern is characterized by the interplanar d-spacing (Å) and the relative intensities ($I/I_o$) of the three strongest peaks in the pattern. The average crystallite size 10.04 nm was determined from the broadenings of corresponding peaks by using the Scherrer's equation $D=k\lambda/\beta (\cos\theta)$.

Where D is the mean crystallite size, k is the grain shape dependent constant 0.89, $\lambda$ is the 1.65 wavelength of the incident beam in nm, $\theta$ is the Bragg reflection angle, and $\beta$ is the line broadening at half the maximum intensity in radians.

Average crystallite size of pure ciprofloxacin calculated from Scherrer's Equation comes out to be 3.22 nm. Nanoparticles containing DEA-EC loaded ciprofloxacin shows amorphous nature due to presence of polymers (FIG. 11) polyvinyl alcohol and DEA-EC, by using Scherrer's equation, particle size comes out to be 10.04 nm.

There are crystal peaks in pure ciprofloxacin XRD pattern from 20-35 2θ values that is characteristic of pure ciprofloxacin sample. X-ray diffraction pattern of Ciprofloxacin loaded NPs showed no crystalline diffraction pattern thus it was concluded that the CP is in the amorphous state.

1.23. Scanning Electron Microscope

Figure 12A:
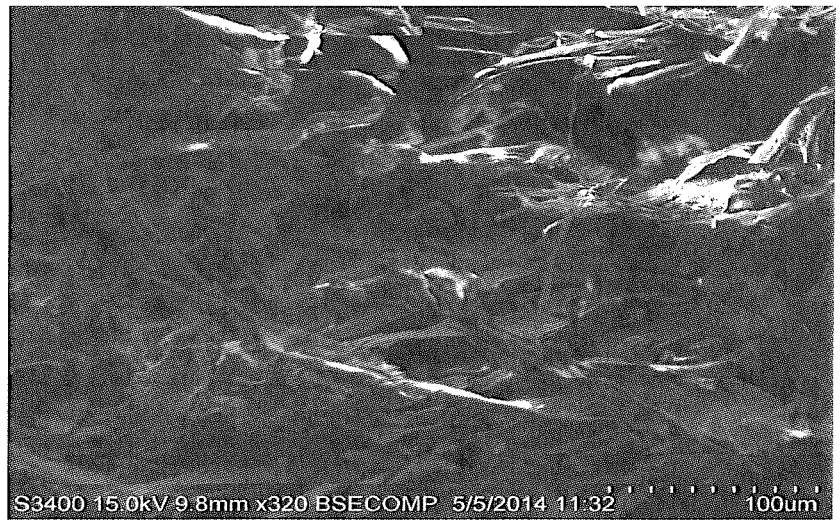
FIGS. 12A and 12B depict SEM images of ciprofloxacin nanoparticles.
Figure 12B:
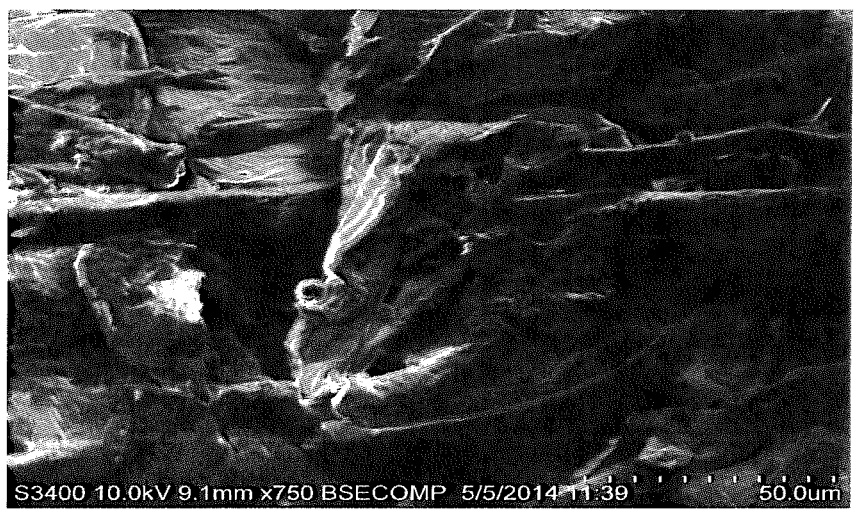

SEM images (FIG. 12) confirm the presence of cross linked polymers that are having entrapped drug in it. Cross linking visible on different scales is DAE-EC polymer that is sustaining releasing polymer.

1.24. GC-Ms

GC-MS analysis of pure ciprofloxacin and ciproloxacin in nanoparticles form was performed using a Shimadzu model 92 QP-2010 instrument. Comprising sampling port and a gas chromatograph interfaced to a mass spectrometer (GC-MS). Samples were prepared by dissolving pure ciprofloxacin in methyl alcohol in one vial and ciprofloxacin nanoparticles DEA-EC loaded in another vial. Sample was injected and run time of 17 minutes was completed and results obtained.

Figure 13A:
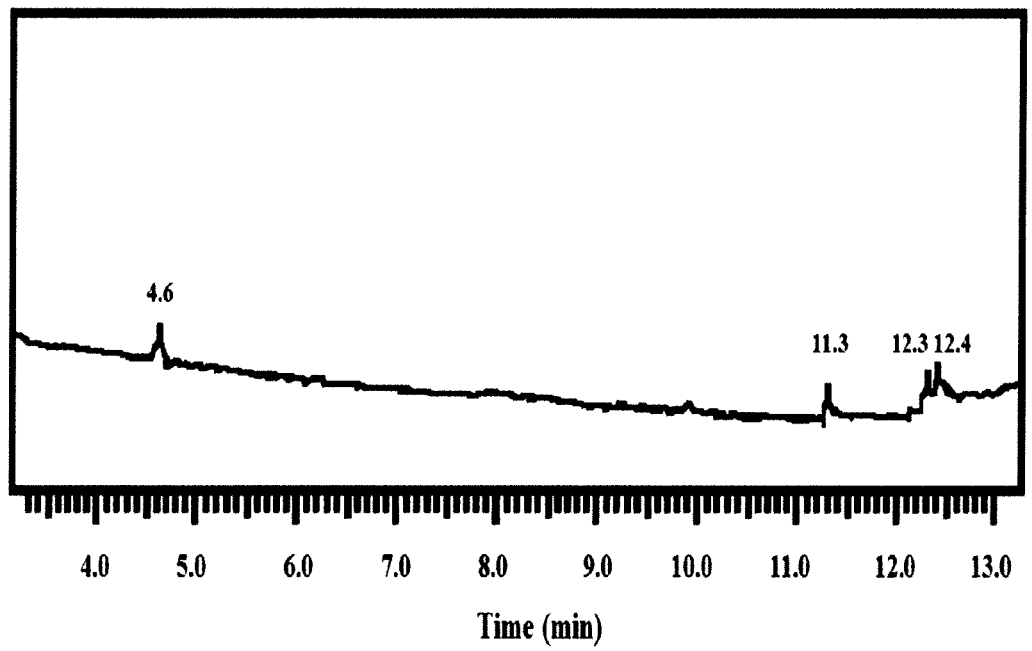
FIG. 13A depicts chromatograph of retention of time pure Ciprofloxacin.
Figure 13B:
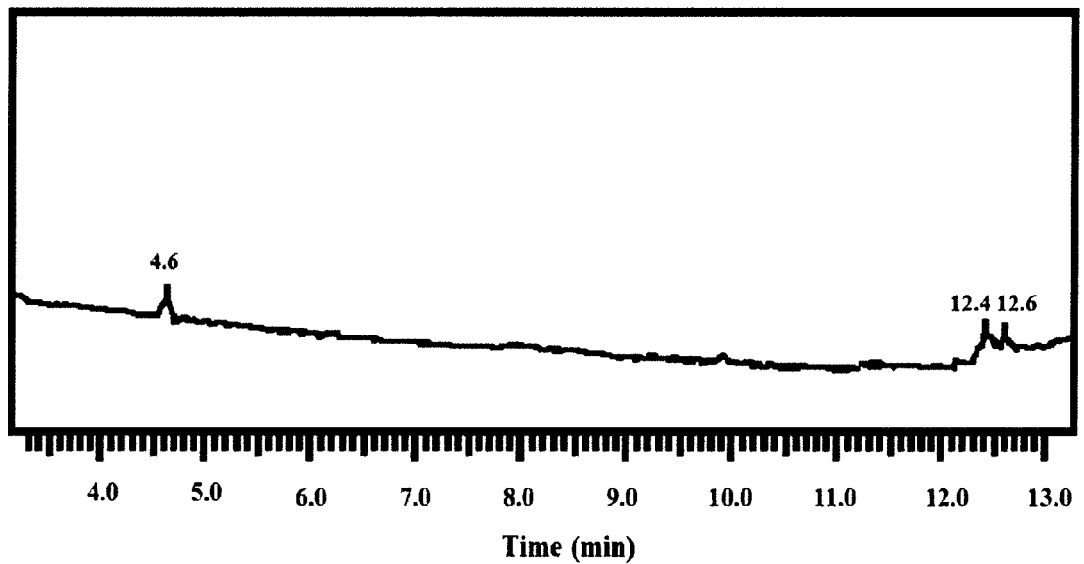
FIG. 13 B depicts Ciprofloxacin nanoparticles.

GC-MS results (FIG. 13A and FIG. 13B) indicate similar fragmentation method. Break down products are similar and retention time 4.621 and 12.4 minutes indicate ciprofloxacin presence in DEA-EC loaded ciprofloxacin nanoparticles. Ciprofloxacin has melting point 265° C. GCMS maximum temperature range was 270° C. DEA-EC has higher melting point so only similar fragmentation patterns of ciprofloxacin in both samples were observe. That confirms the presence of ciprofloxacin in DEA-EC nano form.

1.25. Stability Studies in CSZ Stability Chamber

The objective of these tests is to gather information in order to make recommendations regarding the stability of substances or pharmaceuticals. The ultimate goal is to verify the stability of chemical, microbiological and physical characteristics after exposure to temperature and humidity over a defined period.

CSZ stability chambers are used to test and store a wide range of products in specific temperature and/or humidity conditions. Applications includes half-life testing, stability testing, expiration date testing, accelerated aging and other testing for pharmaceutical, packaging, life science, personal care, medical, biomedical storage, research, and more.

Ciprofloxacin nanoparticles in powder form were placed in closed rubber vial and placed in stability chamber. Ciprofloxacin nanosuspension in another vial was also placed in stability chamber variant conditions were given for six months. Nano suspension form was unstable after one month but powder form remained stable till 6 months. HPLC analysis was done to confirm the integrity of drug during stability studies. Conditions given in variation during 6 months of analysis are summarized as follows:

Long term: 2-8° C., 25° C./60% RH, 25° C./40% RH, 30° C./35% RH or 30° C./65% RH Intermediate: 30° C./65% RH Accelerated: 40° C./75% RH, 25° C./60% RH

1.26. Antibacterial Activity

Antibacterial activity of ciprofloxacin studied a variety of above mentioned microbes in detail. Enhanced activity of ciprofloxacin in nano DAE-EC loaded particles was observed as compared to the conventional market available dosage forms of ciprofloxacin. Disc-diffusion method was employed to study the antibacterial activity.

This method relies on the inhibition of bacterial growth measured under standard conditions. For this test, a culture medium used according to requirements by specific microbes, was uniformly and aseptically inoculated with the test organism and then filter paper discs, which are impregnated with a specific concentration of a particular antibiotic is placed in the medium. Zone of inhibitions were calculated after prescribed incubation period for each microbe for nanosuspension prepared and standard injection of ciprofloxacin available in the market. Enhanced antibacterial activity was observed with nanosuspension contained ciprofloxacin loaded DEA-EC nanoparticles.

TABLE 1

Describes the antibacterial activity

| Bacterial Strain used | GRAM Staining | Medium Used | DEA-EC Loaded Ciprofloxacin NP Zone Of Inhibition (Mm) | Ciprofloxacin Injection In Market Zone Of Inhibition (mm) | Dose Applied (mg/mL) | Conclusion |
|---|---|---|---|---|---|---|
| *Escherichia coli* | Gram negative | Agar medium | 27 | 20 | 4 | Enhanced killing activity |
| *Pseudomonas aeruginosa* | Gram negative | Agar medium | 24 | 18 | 4 | Enhanced killing activity |
| *Salmonella* | Gram negative | Agar medium | 18 | 15 | 4 | Enhanced killing activity |
| *Neisseria gonorrhea* | Gram negative | Chocolate agar medium | 25 | 20 | 4 | Enhanced killing activity |
| *Bacteroidesfragilis* | Gram negative | Brain heart infusion agar medium | 23 | 19 | 4 | Enhanced killing activity |
| *Moraxella catarrhalis* | Gram negative | Brain heart infusion agar medium | 24 | 22 | 4 | Enhanced killing activity |

TABLE 1-continued

Describes the antibacterial activity

| Bacterial Strain used | GRAM Staining | Medium Used | DEA-EC Loaded Ciprofloxacin NP Zone Of Inhibition (Mm) | Ciprofloxacin Injection In Market Zone Of Inhibition (mm) | Dose Applied (mg/mL) | Conclusion |
|---|---|---|---|---|---|---|
| *Chlamydia trachomatis* | Gram negative | Agar medium | 17 | 13 | 4 | Enhanced killing activity |
| Pathogenic staphylococci. | Gram positive | Mannitol salt agar | 14 | 8 | 4 | Enhanced killing activity |
| *Enterobacteraerogenes* | Gram negative | Eosin methylene blue agar | 16 | 13 | 4 | Enhanced killing activity |
| *Salmonella typhosa* | Gram negative | MacConkey's agar | 23 | 19 | 4 | Enhanced killing activity |
| *Shigella flexeneri* | Gram negative | MacConkey's agar | 21 | 18 | 4 | Enhanced killing activity |
| *Streptococcus pyogenes* | Gram positive | Agar media | 23 | 17 | 4 | Enhanced killing activity |
| *Streptococcus pneumoniae* | Gram positive | Agar media | 23 | 18 | 4 | Enhanced killing activity |
| *Bacillus subtilis* | Gram positive | Agar starch media | 21 | 17 | 4 | Enhanced killing activity |
| *Bacillus cereus* | Gram positive | Agar starch media | 23 | 20 | 4 | Enhanced killing activity |
| *Proteus mirabilis* | Gram positive | Agar starch media | 22 | 19 | 4 | Enhanced killing activity |
| *Serratia marcescens* | Gram positive | Agar starch media | 14 | 12 | 4 | Enhanced killing activity |
| *Klebsiella pneumoniae* | Gram positive | Agar starch media | 13 | 9 | 4 | Enhanced killing activity |

Research successfully yielded DEA-EC loaded ciprofloxacin nanoparticles by solvent evaporation method. Morphology and particle size in range of 10 nm determined by SEM and XRD analysis, respectively. Ciprofloxacin nanoparticles were characterized by DSC-TGA, FTIR, UV-Spectrophotometry, HPLC, GCMS, Zeta sizer.

Stability studies were conducted in a stability chamber and results showed significant stability and controlled release profile generated by dissolution studies showing a sustain release of the drug from polymer. Enhanced antibacterial activity was observed against a variety of gram positive and gram negative bacteria.

Nanoparticles, because of their sustained-release properties, sub-cellular size, and biocompatibility with tissue and cells, held promise for the achievement of these objectives.

What is claimed is:

1. A method of preparing ciprofloxacin loaded biodegradable polymeric nanoparticles comprising:
   a. preparing a 1% to 3% solution of diethyl amino ethyl cellulose in ethyl acetate by stirring ethyl amino ethyl cellulose in ethyl acetate for 15 to 25 minutes at medium speed;
   b. adding a 0.2-0.6% aqueous solution of ciprofloxacin, drop by drop, to the solution in step (a) and mixing in an ultrasonic shaker;
   c. adding a 0.5 to 1% aqueous solution of polyvinyl alcohol drop by drop to step (b) solution and emulsifying by subjecting the solution to ultrasonification at 50-70 Hz for 15-25 minutes;
   d. subjecting the solution in step (c) to ultracentrifugation for 5-15 minutes at 10-15,000 rpm; and,
   e. removing the sediment from step (d) and drying at 45-55° C. for 0.5 to 1.5 hours.

2. The method of claim 1, step (a), wherein the concentration of diethyl amino ethyl cellulose is 1.14%.

3. The method of claim 1, step (a), wherein the solution is stirred for 20 minutes.

4. The method of claim 1, step (b), wherein the concentration of ciprofloxacin is 0.4%.

5. The method of claim 1, step (c), wherein the concentration of polyvinyl alcohol is 1%.

6. The method of claim 1, step (c), wherein the solution is subjected to ultrasonification at 50 Hz for 20 minutes.

7. The method of claim 1, step (d), wherein ultracentrifugation is carried out at 13000 rpm for ten minutes.

8. The method of claim 1, step (e), wherein the sediment is dried at 50° C. for one hour.

\* \* \* \* \*